(12) United States Patent
Peng

(10) Patent No.: US 10,167,445 B2
(45) Date of Patent: Jan. 1, 2019

(54) CELL CULTURE MONITORING SYSTEM WITH LOW POWER CONSUMPTION

(71) Applicant: Hong Peng, Fremont, CA (US)

(72) Inventor: Hong Peng, Fremont, CA (US)

(*) Notice: Subject to any disclaimer, the term of this patent is extended or adjusted under 35 U.S.C. 154(b) by 0 days.

(21) Appl. No.: 15/478,188

(22) Filed: Apr. 3, 2017

(65) Prior Publication Data

US 2017/0283760 A1 Oct. 5, 2017

Related U.S. Application Data

(60) Provisional application No. 62/317,644, filed on Apr. 4, 2016.

(51) Int. Cl.
*G01N 33/48* (2006.01)
*C12M 1/00* (2006.01)
*C12M 3/06* (2006.01)
*C12M 1/34* (2006.01)
*G01N 33/483* (2006.01)

(52) U.S. Cl.
CPC ............ *C12M 31/02* (2013.01); *C12M 23/22* (2013.01); *C12M 27/16* (2013.01); *C12M 31/06* (2013.01); *C12M 41/06* (2013.01); *C12M 41/12* (2013.01); *C12M 41/14* (2013.01); *C12M 41/36* (2013.01); *C12M 41/42* (2013.01); *C12M 41/46* (2013.01); *G01N 33/4833* (2013.01)

(58) Field of Classification Search
CPC .... G01N 21/76; G01N 27/301; G01N 27/302; G01N 27/333; G01N 27/36; G01N 1/34; G01N 1/405; G01N 2030/528; G01N 2035/00356; G01N 2035/0486; G01N 21/69; G01N 30/52; G01N 30/6095; G01N 35/025
See application file for complete search history.

(56) References Cited

U.S. PATENT DOCUMENTS

2005/0254055 A1* 11/2005 Peng .................. G01N 21/51
356/432

* cited by examiner

*Primary Examiner* — Michael P Stafira

(57) ABSTRACT

An improved cell culture monitoring system and method that detects cell growth and concentration in a dynamic environment of incubator/shaker. In order to reduce power consumption and make a wireless cell culture monitoring system practical, several methods of temperature compensation are used to replace a method of controlling the temperature of sensing module. Furthermore its power consumption can be significantly reduced by using an adaptive and synchronized light pulse detection technique.

12 Claims, 3 Drawing Sheets

CELL CULTURE MONITORING SYSTEM WITH LOW POWER CONSUMPTION

CROSS-REFERENCE TO RELATED APPLICATION

This patent application claims priority from U.S. Provisional Patent Application Ser. No. 62/317,644, filed on Apr. 4, 2016, which is incorporated by reference herein in its entirety.

BACKGROUND OF THE INVENTION

Apparatuses and methods as described in U.S. Pat. No. 7,339,671, entitled: "Apparatus and Method for Monitoring Biological Cell Culture", presented a system which can perform real time and on-line monitoring of a biological cell culture in an incubator/shaker. Such system employs a light scattering technique to detect biology cell concentration (in form of turbidity or optical density) or other measurable properties of the biological culture medium in a transparent container such as an Erlenmeyer flask. With progress of wireless technologies, internet cloud and smart phone, the invention of this cell culture monitoring system initiated in a decade ago can have some new feasible improvements. When U.S. Pat. No. 7,339,671 was filed a decade ago, a practical way in term of technologies and costs for the cell culture monitoring system was to use wire to power culture detection sensor and temperature control circuit in a sensor head as well as to send measured signal or data to a control module or a computer via an intermediate control module. The sensor head is a sensing device which can be put in an incubator/shaker and can attach to a cell culture medium container in operation. However, wire connection from the sensor head to the control module can be difficult for many existing shakers because of their sealed enclosure for temperature control. Also the shaking environment can make wire connection unstable so that extra care for wire selection and wire arrangement in shakers are required. To overcome the problem of wire connection, wireless embodiment as described in the initial invention has to deal with some critical issues such as power consumption, measurement accuracy and reliable RF wireless connection. For a wireless and battery powered sensor head, the crucial challenge is to monitor biologic cell continuously and accurately for many hours or days in some case without changing or charging the battery.

With respect to the sensor head or probe defined in U.S. Pat. No. 7,339,671, the major power consumption comes from temperature control module and light sensing module. The light sensing module consists of at least one light source such as a LED or laser diode and at least one photodetector such as a photodiode. The radiation intensity of the light source and the sensitivity of the photodetector are temperature dependent. Usually incubator/shaker can operate at a temperature from ambient+5 C to 80 C. To have an accurate measurement in such temperature range, the monitoring system needs temperature control or temperature compensation for its light source and photodetector. A temperature control with peltier element dissipates a lot of electrical power and is not feasible for a battery powered sensor head. Therefore a power saving temperature compensation becomes a necessary method for constructing a wireless sensor head.

Temperature compensation methods for LED, laser diodes and photodetectors have been reported in many patent publications. Some publications such as U.S. Pat. No. 5,761,230 and U.S. Pat. No. 5,974,064 presented analog compensation circuits with temperature sensing thermistor for automatically adjusting current applied to LED and laser diode or adjusting voltage applied to photodetector. This type of temperature compensation is analog and has low power consumption. But it is not easy to find good match in temperature characteristic among thermistors and a variety of LED, laser diode or photodetector for a wide temperature range. Some publication such as EP2664264A1 and U.S. Pat. No. 5,477,576 presented software compensation with pre-measured and pre-calculated temperature coefficients of combined light source and photodetector. Because both light source and photodetector have non-linear relationship with temperature, their superimposed temperature coefficients becomes so complicated that its temperature correction could require 4th degree polynomial regression. Also for different light intensity detected in photodetector, the coefficients of polynomial are different.

In recent years, many wireless technologies (Wifi, Bluetooth, Zigbee, etc) have been used for various wireless applications. The power consumption and reliability for the wireless technologies has been improved. Bluetooth Low Energy (BLE) appears to be a technology with much low power consumption comparing with Wifi and classic Bluetooth. BLE is designed to run for months or years with a button cell battery such as CR2032. With such wireless technology, the major challenges for the wireless cell culture monitoring system are to make accurate measurement without temperature control and to prolong battery life in usage for days or weeks.

The object of this invention is to improve the cell culture monitoring system presented in U.S. Pat. No. 7,339,671 with low power consumption methods and devices. The innovated methods and devices make the cell culture monitoring system with a wireless sensor head feasible and practical. The wireless monitoring system gets rid of the wire connection problem and makes its sensor head to be easily mounted in incubator/shakers. Furthermore, the wireless monitoring system enables it to be easily integrated with not only PCs but also modern wireless devices such as smart phones and tablets.

SUMMERY OF THE INVENTION

This invention presents a plurality of embodiments to improve the cell culture monitoring system with a wireless sensor head. In one aspect, without temperature control for the light sensing module, a method of two step temperature compensations are used to improve over all measurement accuracy of the cell culture monitoring system. The two step compensations comprise 1) a solely analog circuit or an analog circuit controlled by a microprocessor to reduce light intensity variation of light source due to temperature change and 2) a microprocessor to make a correction on final detection signal such as turbidity or optical density (OD) with pre-measured, pre-calculated and saved temperature coefficients. In another aspect, the power consumption in the sensor head can be significantly reduced with a method that the light source is controlled by a light driving pulse signal which has a low duty cycle. Using this method, the time and duration of turning on the light source are synchronized with trigger pulses for data acquisition in A/D converter. Instead of a fixed duty cycle or fixed time duration of tuning off the light source, the time duration of tuning off the light source can be adaptive to cell culture growth level and growth rate.

As an example, the turning off time duration can change with the change of cell culture turbidity or turbidity change rate.

DESCRIPTION OF THE INVENTION

Figure 1:
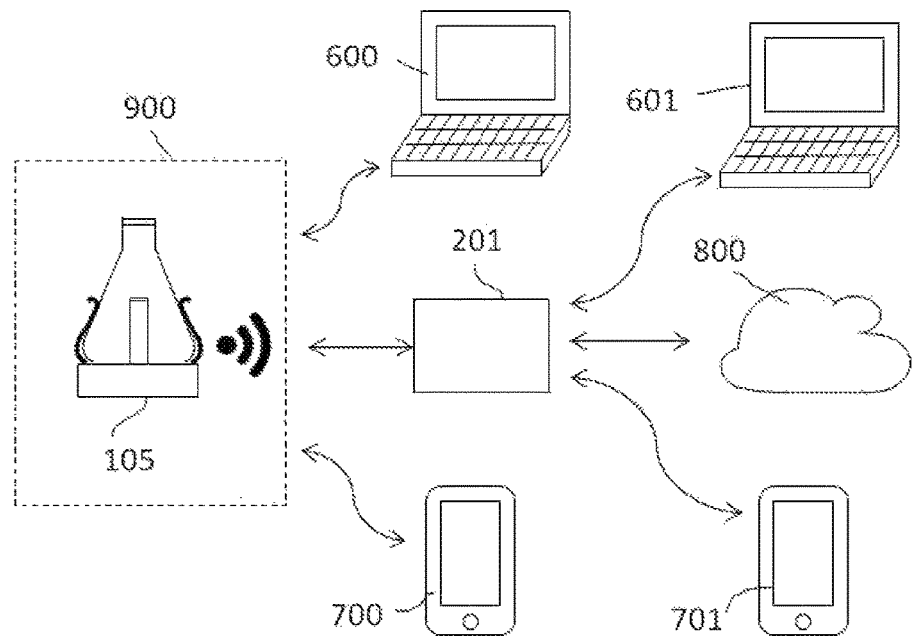
FIG. 1. A schematic diagram of a standalone cell culture monitoring system with a wireless sensor head for flask biological culture applications.

New development in wireless and IoT (Internet of Thing) technologies provides opportunities for improving the cell culture monitoring system described in U.S. Pat. No. 7,339,671. FIG. 1 shows one embodiment of such improved cell culture monitoring system. Sensor head 105 of the cell culture monitoring system can be a wireless probe which includes at least one wireless transceiver, A/D and D/A converter, microprocessor, temperature sensor, motion sensor, memory and battery. In one embodiment, battery can be a separated part which is not mounted in the sensor head enclosure. The battery can be mounted outside or attached to sensor head 105 with power supply wires. Sensor head 105 has basic functions for monitoring cell culture medium such as scattering light intensity, turbidity or OD and sending data wirelessly to other devices such as a control module 201 outside of incubator/shaker 900. In one embodiment, sensor head 105 and module 201 compose a standalone cell culture monitoring system. Module 201 can be a user interface device which has at least a wireless transceiver, microprocessor, memory, LCD display, alarm and keypad/button. Module 201 can perform data process, data storage, data display, calibration and control of the cell monitoring system. In one option, module 201 can also be a networked device via DSL or Wifi or other technologies so that module 201 can be controlled by other computer 601 or smart device 701 such as smart phone and the data from module 201 can be put in cloud 800 and shared by other devices. In some embodiments, module 201 is replaced by a computer 600 or a smart device 700. Sensor head 105 can directly connect to a computer 600 or smart device 700 via Bluetooth or other wireless technology. With help of software, computer 600 or smart device 700 can not only process and display the data from probe 105 but also control the data acquisition of sensor head 105 like module 201 does. Because a motion sensor and temperature sensor are built in sensor head 105, module 201, computer 600 or smart device 700 can show and record not only the culture turbidity/OD but also the orbital rotation speed of incubator/shaker 900 as well as cell culture temperature.

Figure 2:
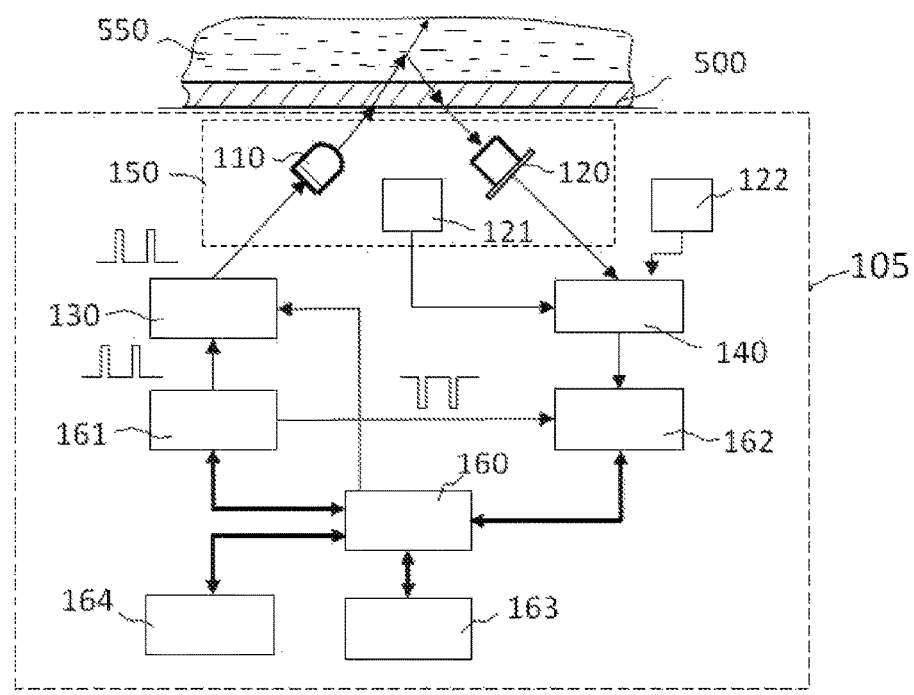
FIG. 2 A schematic and block diagram of a wireless sensor head.

In one embodiment, wireless sensor head 105 as shown in FIG. 2 comprises sensing module 150, light source drive circuit 130, sensing circuit 140, temperature sensor 121, motion sensor 122, pulse circuit 161, A/D converter 162, microprocessor 160, wireless transceiver 163 and memory 164. The data collected and processed by microprocessor 160 can be transmitted to module 201, computer 600 or smart device 700 through a wireless transceiver 163. Module 201, computer 600 or smart device 700 can also send command to sensor head 105 through transceiver 163. FIG. 2 doesn't show a plurality of light sources, photodetectors, MCUs, and A/D converters, etc for the sake of description simplification. However in some embodiments, a plurality of component devices such as light source 110, photodetector 120 and A/D converter 162 can be used in sensor head 105.

Sensing module 150 is a key part of sensor head 105. Module 150 comprises at least one light source 110, at least one photodetector 120 and at least one temperature sensor 121. To have fast (low time constant) and accurate temperature measurement of light source 110 and photodetector 120, in one embodiment, module 150 comprises a good thermoconductive housing for light source 110, photodetector 120 and temperature sensor 121. Temperature sensor 121 is positioned between light source 110 and photodetector 120 so as to have accurate temperature measurement of the both devices. Sensing module 150 is also designed to align the radiation beam of light source 110 and the sensing area and wavelength of photodetector 120 for scattering light detection of cell culture medium 550. For such reason, module 150 can comprise collimators, lens and optical filter to avoid or reduce light reflection influence of culture medium container 500 such as a flask.

Figure 3:
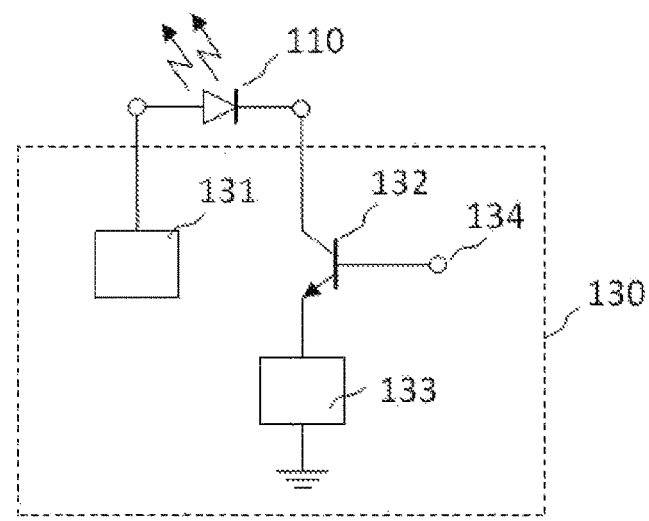
FIG. 3 A schematic and block diagram of light source driving circuit.

Without temperature control, the light intensity of light source 110 such as a LED or a laser diode changes with the change of temperature. Light source drive circuit 130 becomes an important part of this invention for temperature compensation and power conservation. FIG. 3 shows one embodiment of light source drive circuit 130 which comprises power supply 131, transistor 132 and current control circuit 133 for temperature compensation. Input port 134 is connected to a pulse supply circuit 161. A high voltage pulse input at port 134 turns on light source 110 and light source 110 is in "light-on" status. A low or zero voltage input turns off light source 110 and light source 110 is in "light-off" status. Power supply 131 is a constant DC voltage supply. Because the output voltage of battery decreases with its usage, power supply 131 can have a step up or down regulator to keep the output DC voltage to be constant. Transistor 132 can be any kind of transistors such as BJT, JFET and MOSFET. Current control circuit 133 for temperature compensation can use different techniques. The technique can be different for LED or laser diode. For a laser diode, its lasing threshold current and output power is temperature dependent. The lasing threshold increases and the output power decreases when temperature increases. There are some circuit methods for temperature compensation. The popular one is to use a photodiode to detect the output power of the laser diode and then make adjustment of driving current to the laser diode automatically. This method is widely used in laser pointer. However this APC control can't compensate the change of the lasing threshold current. Another method is to use a thermistor circuit to control the driving current of the laser diode. The principle is that a selected thermistor can have approximately same exponential temperature characteristic as that of the lasing threshold current of the laser diode. This analog method can make the temperature compensation less complicated and also having a wide temperature range.

In one embodiment of this invention, current control circuit 133 can use a thermistor circuit method for the temperature compensation of light source 110, especially for laser diode. Besides solely analog circuit current control, in another embodiment, current control circuit 133 is controlled by microprocessor 160 based on the measurement input of temperature sensor 121. Generally, microprocessor 160 makes a variable voltage output via its DAC port to circuit 133. In this case, circuit 133 is a voltage controlled current source. Microprocessor 160 has a pre-saved compensation function of the driving current of light source 110 versus temperature for a specific and constant output power of light source 110. This method can be used for both LED and laser diode. FIG. 3 discloses just one embodiment of light driving circuit 130 with both pulse switching on/off and temperature compensation capabilities. To those skilled in the art, there are many circuit designs which can have both pulse switching on/off and temperature compensation capabilities.

Although light driving circuit 130 and sensing circuit 140 use some techniques to make temperature compensation, a further step of temperature compensation technique is needed to improve over all optical detection accuracy of the cell culture monitoring system. This second step of temperature compensation is accomplished by microprocessor 160 and software. In one embodiment, microprocessor 160 and memory 164 are used to store a plurality of pre-measured and pre-calculated temperature coefficients for an array of different turbidity of standard medium. Those temperature coefficients are superimposed coefficients of photodetector 120 and light source 110 with circuit compensation. Because the light source 110 has already had a circuit temperature compensation, the temperature coefficients can be obtained with $2^{nd}$ degree polynomial regression instead of $4^{th}$ degree polynomial regression from measured turbidity of a standard turbidity medium at different temperature. To cover a full range of turbidity of culture medium, an array of standard medium such as Formazin with various turbidity values need to be measured at different temperature using sensor head 105. With those pre-stored coefficients, microprocessor 160 can calculate a correction for the output signal of photodetector 120 based on measured temperature from temperature sensor 121 and turbidity detected from culture medium. This two step temperature compensation technique is different from existing one step techniques.

Figure 4:
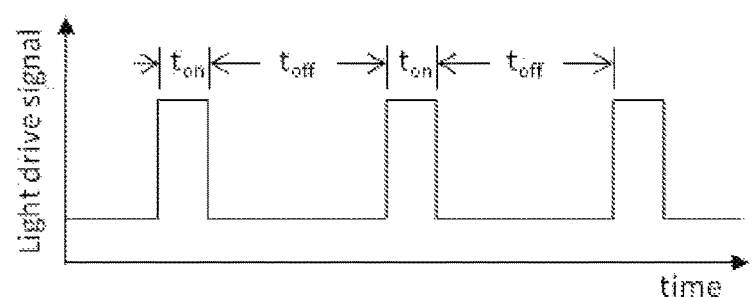
FIG. 4 A schematic diagram of a basic light driving pulse signal with a constant duty cycle.
Figure 5:
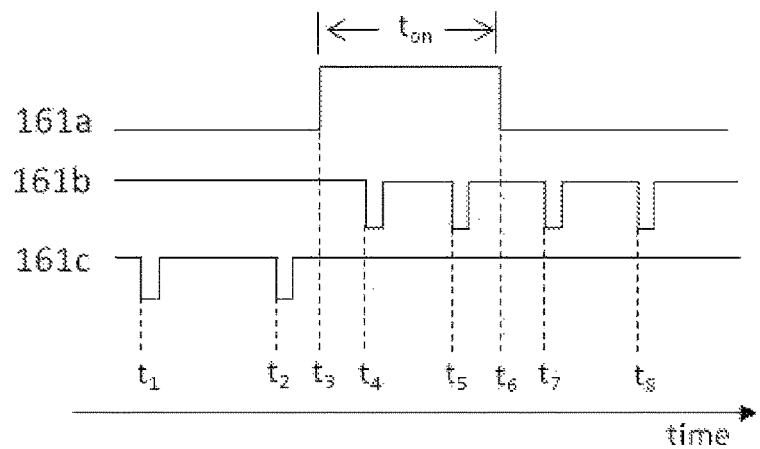
FIG. 5 A schematic diagram of time sequence of light driving signal and pulse triggers for A/D conversion.

Pulse generation circuit 161 is controlled by microprocessor 160. In one embodiment, circuit 161 can comprise part of digital I/O of microprocessor 160 and a crystal oscillator/clock for pulse and trigger synchronization. The basic function of circuit 161 is to generate a low duty cycle pulse as shown schematically in FIG. 4 to drive light source 110. Then drive light source 110 can generate pulsed light based on the driving signal. In one embodiment, the light driving signal has a constant and preset period. The period is equal to the sum of one cycle of light-on time duration $t_{on}$ and light-off time duration $t_{off}$ (period=$t_{on}$+$t_{off}$). Because cell culture process in incubator/shaker can take many hours and the change of scattering turbidity of culture medium 550 is slow, the duty cycle can be set to low level. For instance, $t_{on}$=1 s and $t_{off}$=19 s, its duty cycle is 5%. This means 95% power can be saved in comparison with a continuous driving light source 110 in prior state of the art without a power saving issue. To conserve power, bandwidth and memory, in one embodiment, A/D converter 162 is externally triggered by pulses from generator 161. The A/D converter 162 starts analog to digital conversion after receiving the first trigger and stops the conversion after receiving the second trigger. A/D converter 162 can include multiple A/D converters for light signal, temperature signal and motion signal. In one embodiment, pulse circuit 161 generates light driving signal and a plurality of trigger pulses in a sequence as shown in FIG. 5. This sequence occurs in each light-on and light-off cycle. Pulse 161a is the light driving signal. Pulse 161b is a trigger signal for photodetector signal A/D conversion. When light source 110 is on, time $t_4$ starts A/D conversion and time $t_5$ stops A/D conversion. There is always a delayed time ($t_4$-$t_3$) to allow the output power of light source 110 to be stabilized after it is switched on at $t_3$. When light source 110 is switched off at $t_6$, shortly, time $t_7$ starts A/D conversion and time $t_8$ stops A/D conversion. When light is off, the photodetector signal during the time of $t_7$-$t_8$, can be used to subtract common noise like ambient light or electrical noise from the light-on signal. Pulse 161c is a trigger signal for A/D conversion of both temperature and motion signal. This conversion occurs shortly before the light source is tuned on. Time $t_1$ starts A/D conversion and time $t_2$ stops A/D conversion. The temperature measured in duration t1-t2 can be used for the temperature compensation of following light signal measurement in duration $t_4$-$t_5$. This is critical for the low duty cycle pulse method. Generally, duty cycle can be preset and changed by changing the duration $t_{off}$. Duration $t_{on}$ is kept to be constant so that all trigger times (t1, t2, t4, t5, t7 and t8) relative to t3 and t6 are fixed. This sequence is synchronized with a clock. All data acquisition of light signal, temperature and motion are timely stamped and can be saved in memory 164 or memory in control module 201.

Sensing circuit 140 comprises low noise amplifiers and signal conditioning circuit for photodetector 120, temperature sensor 121 and motion sensor 122. Circuit 140 may have differential amplification design which uses a second photodetector as reference to reduce temperature caused drift in output signal. The second photodetector is placed near the first photodetector 120 so that they always have the same temperature. The second photodetector with the same characteristic specs of photodetector 120 is isolated from sensing incident light.

Wireless transceiver 163 can be constructed with different wireless technologies which are Bluetooth, BLE, Zigbee, or proprietary wireless technology such as ANT. In one embodiment, wireless transceiver 163 is constructed with BLE (Bluetooth Low Energy). Because the power consumption of BLE is low for the cell culture monitoring application. Also piconet of BLE allows control module 201, computer 600 or smart device 700 to control and monitor up to eight of sensor heads 105.

Figure 6:
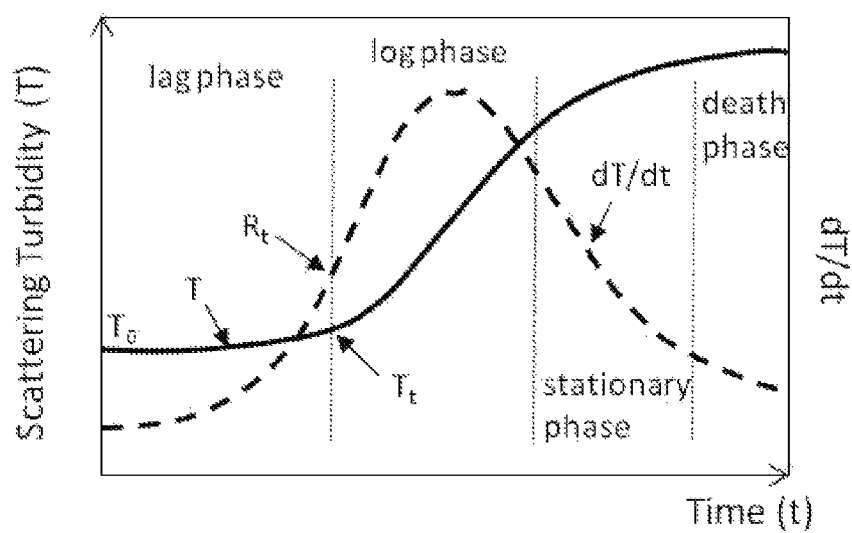
FIG. 6 Typical growth curve and growth rate in term of the scattering turbidity of biological culture.

For batch microbial culture such as shaking flask culture, biological cells such as microorganisms experience typical four phases as shown in FIG. 6, lag phase, log phase, stationary phase and death phase. In the lag phase, microorganisms grow slowly and are acclimated to their new habitat. In the log phase, the number of microorganisms increases exponentially. In the stationary phase, the viable number of microorganisms becomes stabilized. In the death phase, the viable number of microorganisms decreases. The different biological cells, their growth rate or curves can be different at different shaking speed or temperature. Based on this fact, in some embodiments, the duration of light-off $t_{off}$ can be adaptive to the growth curve or growth rate of biological cells instead of having a preset and fixed period of the pulse for turning on/off light source 110. This means that the pulse period is a variable which depends on the biological cell growth level or growth rate. In one embodiment, $t_{off}$ adjustment is based on the change of calibrated scattering turbidity (T). In another embodiment, $t_{off}$ adjustment can be based on the change of culture medium OD. In another embodiment, $t_{off}$ adjustment can be based on light intensity change detected by photodetector 120 such as the voltage output of photodetector amplifier. In this case, the monitoring system doesn't need to convert photodetector output to turbidity or culture OD. In following embodiment description, only turbidity is mentioned. However the photodetector signal output or culture OD can also be used similarly for the adjustment of light-off duration $t_{off}$.

With respect to the $t_{off}$ adjustment, in one embodiment, the maximum light-off duration $t_{max}$ and the minimum duration $t_{min}$ need to be defined and preset before cell culture process. The cell culture will start with $t_{max}$. In one simple option, the duration $t_{off}$ can change from $t_{max}$ to $t_{min}$ when a growing turbidity value reaches a preset threshold turbidity $T_t$ as shown in FIG. 6, for example, such as 120% of initial turbidity value $T_0$ when cell culture starts. After $t_{off}$ reaches $t_{min}$, light-off duration $t_{off}$ will keep the value of $t_{min}$ in the rest of cell culture process. In another option, the light-off duration $t_{off}$ can be a linear function of the turbidity T before the turbidity reaches threshold turbidity $T_t$ and $t_{off}$ becomes $t_{min}$ as shown in equation, $$t_{off} = t_{max} - \frac{T - T_0}{T_t - T_0}(t_{max} - t_{min})$$

where $T_0$ is an initial turbidity of the culture medium. In this case, the light-off duration $t_{off}$ will also keep the minimum duration $t_{min}$ even the cell culture is in stationary and death phase. To address this drawback and prolong light-off duration $t_{off}$ in the stationary and death phase, in one embodiment, the light-off duration $t_{off}$ can change according to turbidity change rate dT/dt as shown in FIG. 6. In the same simple ($t_{max}$ or $t_{min}$) option, the sleep time interval will change from $t_{max}$ to $t_{min}$ when the turbidity change rate dT/dt is equal to or larger than a preset threshold rate $R_t$. When cell growth rate decreases and turbidity change rate dT/dt drops below the threshold rate $R_t$ or a different rate, the light-off duration $t_{off}$ will switch back from $t_{min}$ to $t_{max}$ again. In another embodiment, light-off duration $t_{off}$ changes when the turbidity rate dT/dt changes, $t_{off}=t_{max}-C^*dT/dt$, where C is a preset coefficient which makes $C^*dT/dt$ always less than $t_{max}$. When cell culture starts, dT/dt=0, $t_{off}=t_{max}$. In one option, light-off duration $t_{off}$ keeps to be the minimum limit $t_{min}$. When ($t_{max}-C^*dT/dt$) is equal to or less than $t_{min}$.

Motion sensor 122 can be an accelerometer or a vibration sensor. In one embodiment, an accelerometer is used for measuring the shaking speed of incubator/shaker 900. The shaking speed information can be used for power conservation of sensor head 105. A shaking Incubator/shaker 900 can be stopped or suspended often for various reasons such as making manual OD measurement, adding drug, or adding another culture flask, etc. When the shaking speed becomes zero during a shaking cell culture process, the operation of turbidity detection in sensor head 105 can be suspended until the incubator/shaker starts to shake again. During the suspension, there is no light emission from the light emission source and there is no the A/D conversion for the photodetector.

While the invention has been described in conjunction with the preferred embodiments, features and methods, it should be noted that many alternatives, novel features, novel combination, modifications and variations are apparent to those skilled in the art. Accordingly, the preferred embodiments and description in the invention set forth above are intended to be illustrative and not limiting. Various changes may be made without departing from the spirit and scope of the application.

What is claimed is:

1. A method for reducing power consumption and wirelessly monitoring biological cell culture medium in a dynamic environment of a biological culture incubator/shaker, comprising:
   utilizing a container to hold a liquid biological culture medium in which biological cells are incubated, and at least a part of the container's wall is optically transparent;
   positioning a light emission source relative to the transparent wall of said container and irradiating light through the wall of said container and interacting with said biological culture medium;
   positioning and aiming at least one photodetector to detect light from the interacting section of the incident light with the biological culture medium;
   positioning at least one temperature sensor close to said light emission source and said photodetector;
   providing temperature compensation means for improving measurement accuracy without a temperature control of said light emission source and said photodetector, said temperature compensation means includes steps for controlling the driving current of the light emission source, and then pre-measuring, pre-calculating and pre-storing superimposed temperature coefficients of the controlled light emission source and the photodetector, and then correcting the measurable property values of the biological cell culture medium based on measured temperature of the light emission source and the photodetector and measured turbidity of the cell culture medium;
   providing processing means for amplifying electrical signal from the photodetector, and for processing the signal and presenting properties of the biological cell culture medium.

2. A method of claim 1, wherein said monitoring biological cell culture medium includes monitoring turbidity or/and OD of biological culture medium, wherein the properties include the turbidity and OD.

3. A method of claim 1, wherein said monitoring biological cell culture medium includes monitoring biological cell growth curve and growth rate.

4. A method of claim 1, wherein further providing at least one motion sensor for measuring shaking speed of the incubator/shaker.

5. A method of claim 1, wherein said processing means further includes processing motion sensor signal and presenting the shaking speed of the incubator/shaker.

6. A method of claim 1, wherein said processing means further includes steps for suspending light emission from the light emission source and A/D conversion for the photodetector signal when the shaking speed is below a specific value during a shaking cell culture process.

7. A method of claim 1, wherein said light source drive circuit consists of at least one transistor and one current control circuit.

8. A method of claim 1, wherein further generating a low duty cycle pulse signal with a light source drive circuit to drive said light emission source.

9. A method of claim 8, wherein said generating a low duty cycle pulse signal means making the light-on and light-off time durations of the light emission source to be preset constants.

10. A method of claim 8, wherein said generating a low duty cycle pulse signal means making the light-off time duration adaptive to measured cell culture turbidity or turbidity change rate.

11. A method of claim 8, wherein said generating a low duty cycle pulse signal means making the light-off time duration adaptive to measured cell culture OD or OD change rate.

12. A method of claim 8, wherein said processing means further includes making synchronized A/D conversion for multiple signals in respect to the light-on and light-off time of the light driving pulse signal.

* * * * *